United States Patent
Papirov et al.

(10) Patent No.: US 11,395,666 B2
(45) Date of Patent: Jul. 26, 2022

(54) BALLISTIC SHOCKWAVE FOCUSING WAVEGUIDE

(71) Applicant: HI IMPACTS LTD., Petach Tikva (IL)

(72) Inventors: Eduard Papirov, Hod Hasharon (IL); Itzhak Friedman, Kiryat Ono (IL); Yehoshua Dolberg, Raanana (IL)

(73) Assignee: HI IMPACTS LTD., Petach Tikva (IL)

( * ) Notice: Subject to any disclaimer, the term of this patent is extended or adjusted under 35 U.S.C. 154(b) by 747 days.

(21) Appl. No.: 16/313,477

(22) PCT Filed: Jun. 28, 2017

(86) PCT No.: PCT/IL2017/050721
§ 371 (c)(1),
(2) Date: Dec. 27, 2018

(87) PCT Pub. No.: WO2018/002929
PCT Pub. Date: Jan. 4, 2018

(65) Prior Publication Data
US 2019/0380727 A1    Dec. 19, 2019

Related U.S. Application Data

(60) Provisional application No. 62/355,337, filed on Jun. 28, 2016.

(51) Int. Cl.
*A61B 17/22* (2006.01)
*A61H 23/00* (2006.01)

(52) U.S. Cl.
CPC ..... *A61B 17/22004* (2013.01); *A61H 23/008* (2013.01); *A61B 2017/22024* (2013.01); *A61H 2201/1409* (2013.01); *A61H 2201/1654* (2013.01)

(58) Field of Classification Search
CPC .... A61B 17/22004; A61B 2017/22024; A61H 23/008; A61H 2201/1409; A61H 2201/1654
See application file for complete search history.

(56) References Cited

U.S. PATENT DOCUMENTS

| | | | | |
|---|---|---|---|---|
| 5,160,336 A * | 11/1992 | Favre | ........ | G10K 9/10 606/128 |
| 8,099,154 B1 * | 1/2012 | Wess | ........ | A61B 17/2258 600/427 |
| 2003/0060736 A1 * | 3/2003 | Martin | ........ | A61B 8/4272 601/2 |
| 2011/0054367 A1 * | 3/2011 | Schulz | ........ | A61H 23/0218 601/46 |
| 2015/0161982 A1 * | 6/2015 | Laugharn, Jr. | ........ | G10K 11/28 367/138 |

* cited by examiner

*Primary Examiner* — Hien N Nguyen
(74) *Attorney, Agent, or Firm* — The Law Office of Joseph L. Felber

(57) ABSTRACT

A waveguide that is configured to focus ballistic shockwaves by harnessing the propagation speed of an acoustic wave through different materials by controlling the geometry and the materials forming the waveguide through which the ballistic shockwave is travelling so as to focus the ballistic shockwaves at a focal zone.

20 Claims, 3 Drawing Sheets

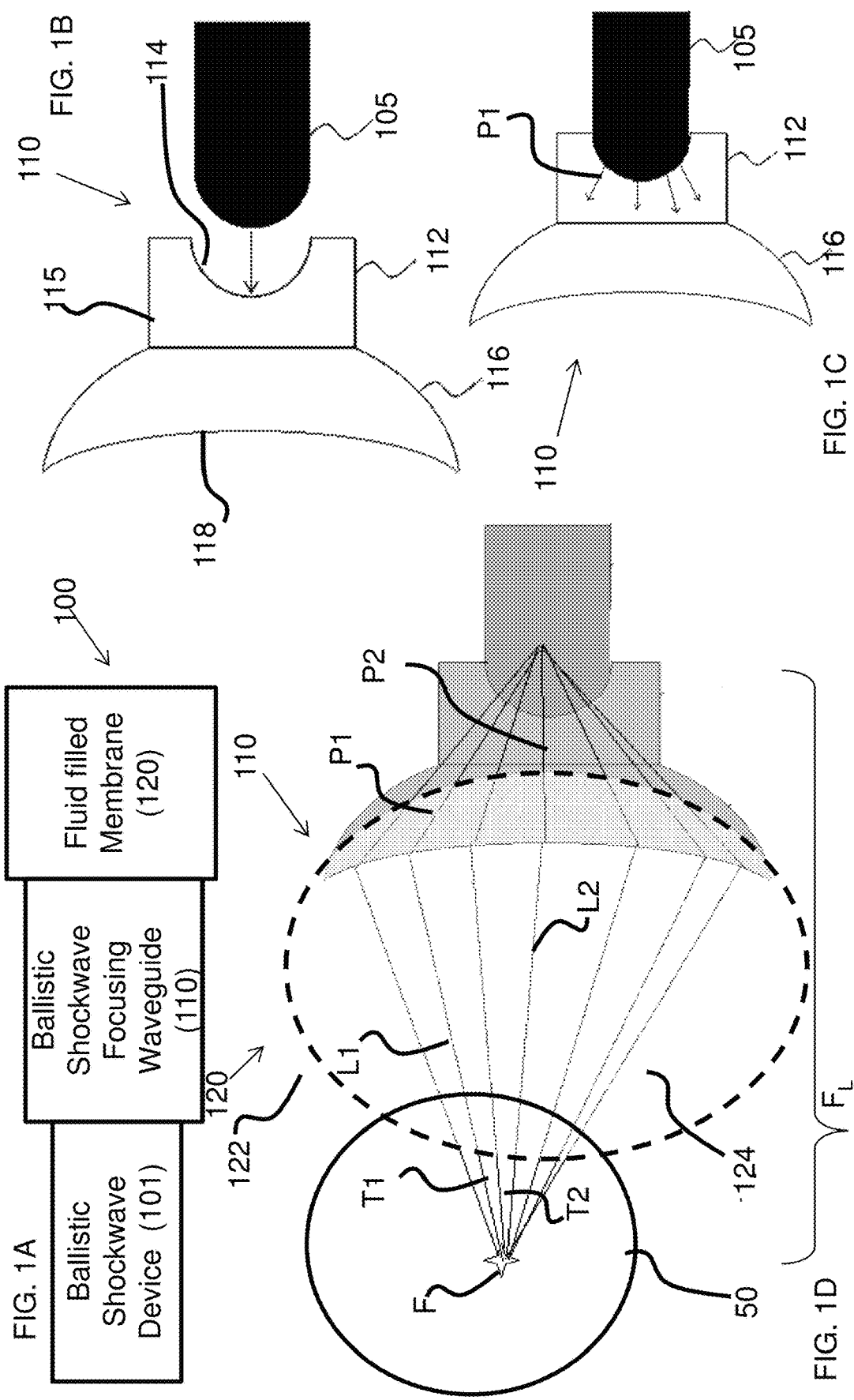

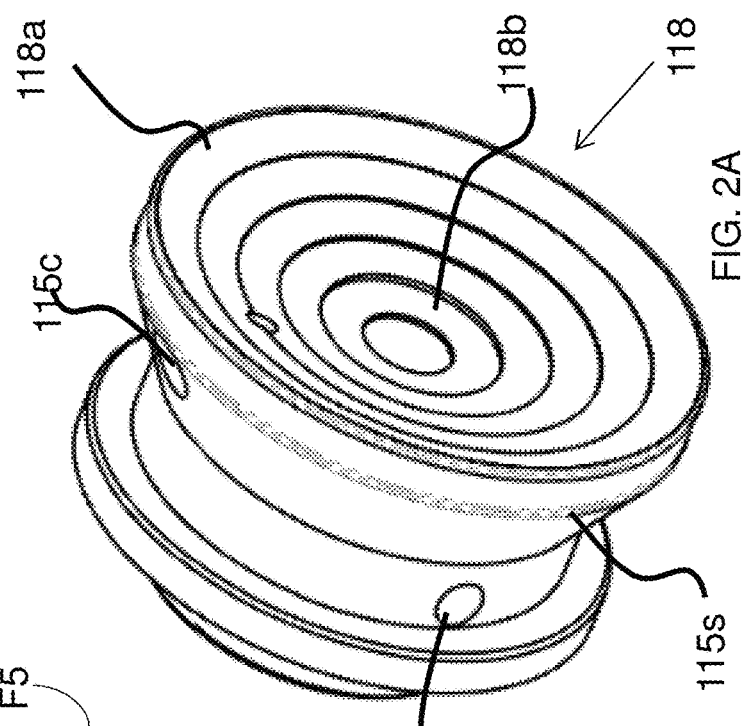
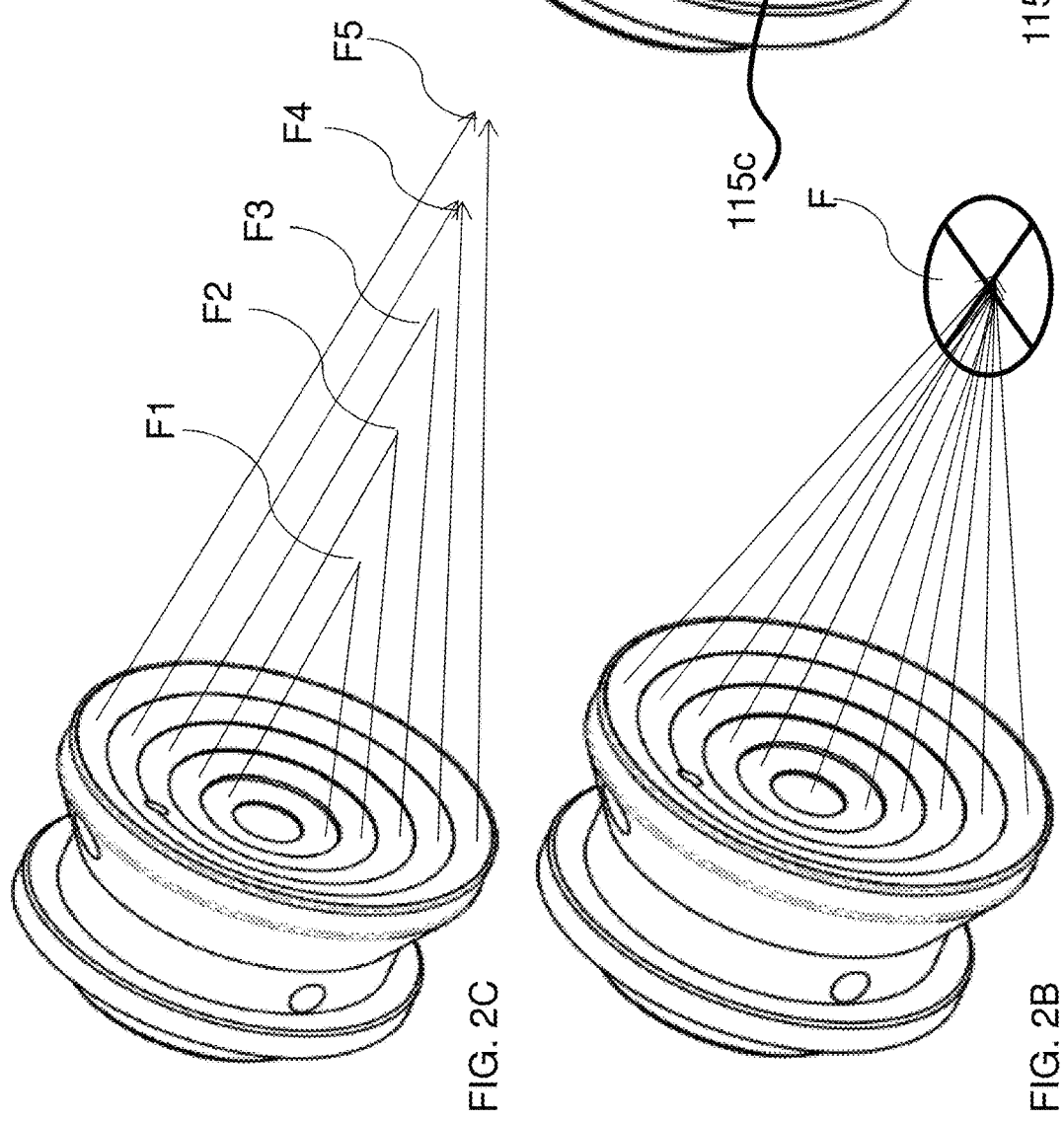

BALLISTIC SHOCKWAVE FOCUSING WAVEGUIDE

CROSS REFERENCE TO RELATED APPLICATION

This application claims the benefit of International Patent Application No. PCT/IL2017/050721, filed Jun. 28, 2017 and entitled "Ballistic Shockwave Focusing Waveguide" which claims priority to U.S. Provisional Patent Application No. 62/355,337 filed Jun. 28, 2016, entitled "Focusing and Coinciding Shockwaves Shaper". The present application incorporates herein by reference the disclosures of each of the above-referenced application in their entireties.

FIELD OF THE INVENTION

The present invention relates to a device for ballistic shockwaves and in particular to such a device, system and method for a waveguide for focusing ballistic shockwaves.

BACKGROUND OF THE INVENTION

Shockwave therapy (SWT) is a non-invasive form of treatment for various medical conditions using acoustic Shockwaves. The use of shockwaves is perhaps best known for its use in fragmentation of kidney stones in a process called lithotripsy. However shockwaves have also been used for other indications such as healing bone fractures, chronic orthopedic inflammation, wound healing of chronic wounds, treatment of heart muscle ischemia as well as other medical condition as is known in the art.

Acoustic Shockwaves may be generated by a variety generators, including electrohydraulic, electroconductive, electromagnetic, piezoelectric and ballistic force generators.

In ballistic shockwave generators, shockwaves are generated by high-energy collisions between two masses, with the energy propagating through a metallic media that is propagated toward the treated biological tissue.

Shockwaves generating devices and system are generally coupled with the tissue being treated with fluid coupling such as gel or a fluid filled bladder so as to allow for the generated shockwaves to enter the target tissue.

Shockwaves are distinct from ultrasound and mechanical pressure waves in that shockwaves have specific characteristics. A pressure wave is a general term for a pressure disturbance moving through a medium. This happens to be exactly what a sound wave is. These disturbances move at the speed of sound in the medium in which they are traveling. There is no formal distinction between the two, as any amplitude of pressure wave could be heard as sound provided the listening device is sensitive enough.

A shockwave however has a specific type of pressure disturbance moving through a fluid medium. For small amplitudes, sound pressure waves pass through the medium, which then more or less returns to its initial state. However, a wave with large enough amplitude will drag a little bit of the medium along with it. That means that sound waves propagating behind it will tend to catch up with the original wave and drag the fluid behind them still faster. That process stacks up and eventually you can have a number of pressure waves that coalesce into a shockwave.

Although sharing several common properties, shockwaves differ from mechanical pressure waves in the important feature of pulse duration. The energy wave front of true shockwaves is concentrated within several microseconds (0.25 to 4 microseconds, when measured according to IEC61846 and commonly between 0.5-1 microsecond), while the energy of a pressure wave is dispersed over several milliseconds (1 to 7 milliseconds, regularly). A shockwave pulse has a rise-time of 300 nanoseconds occurs within 1 microsecond from pulse start and a mechanical pressure pulse starts approximately 1 millisecond later.

This distinction between mechanical pressure waves and shockwaves determines the penetration of the wave energy; while mechanical pressure waves mainly affect the surface tissue, the short duration of the pressure pulse of shockwaves has limited interaction with surface tissue and the shockwaves energy propagates into the tissue and has more effect on inner body structures.

Focusing shockwave has been accomplished in different way based on the origin of the shockwave that is the shockwave generating device. Electrohydraulic shockwave generating devices utilize elliptic mirrors and reflectors to reflect a plurality of pressure waves to a predefined focal zone where the pressure waves are allowed to coalesce to form a shockwave at a predefined and controllable focal zone.

Electromagnetic shockwave generating devices generate a linear wave front of pressure waves that are focused to a predetermined and controllable focal zone utilizing an acoustic lens.

Piezoelectric shockwave generating devices generating device utilizing a radial arrangement of a plurality of piezoelectric elements to focus the plurality of generated pressure waves that coalesce to form a shockwave at a given focal zone. The focal zone determined by the geometry of the radial arrangement.

SUMMARY OF THE INVENTION

The prior art shockwave focusing means cannot be used for focusing ballistic shockwaves because of the manner in which the ballistic shockwave is generated. Non-ballistic forms of shockwave generation may be focused with the means discussed above because the shockwave is generated within the aqueous propagating medium that includes Ballistic shockwaves are generated due to a collision between two objects the generated energy must be transferred from the collision zone to an aqueous medium in order to allow it to penetrate biological tissue. Accordingly the generated shockwave must be transfer from a non-aqueous environment, generally metal, from the collision zone, to an aqueous environment so as to enable it to be transmitted to biological tissue.

Prior art focusing devices utilizing non-ballistic shockwave generating devices do not require the transfer from a non-aqueous environment to an aqueous environment. Specifically the shockwaves are generated and propagated within the same aqueous environment and/or medium, for example as with electrohydraulic reflectors.

Accordingly there is an unmet need for, and it would be highly useful to have, a device for focusing shockwaves generated with a ballistic shockwave system, and in particular to a waveguide for focusing ballistic shockwaves for extracorporeal shockwave treatment.

Focusing acoustic waves generated by a ballistic shockwave device may be accomplished by controlling the pathway travelled by an acoustic wave through different materials and/or media and/or phases such as solid and/or liquids. The pathway of the ballistic shockwaves may be routed to a specific focal zone. Specifically, the acoustic pathway of a ballistic shockwave may be controlled by harnessing the acoustic velocity (speed of sound) of a sound wave travelling through different materials, solids and/or liquids, and by controlling the geometry of the material through which the acoustic wave is travelling so as to ensure that a generated ballistic shockwave reaches a focal zone within a predefined time window so as to form a focal zone where acoustic shockwaves are concentrated.

The pathway may be further routed and/or controlled by utilizing an implementation and an adaptation of Snell's law of refraction that would allow for controlling and/or predicting the pathway travelled by an acoustic shockwave signal as it transitions through different media, solid and liquids.

Specifically, acoustic energy, for example shockwaves, travel at a constant velocity (V1) through different materials. The velocity is dependent on the material properties and phase. For example materials in solid phase allow acoustic waves to travel faster rather than materials in a liquid phase, for example as outlined in the table below.

TABLE 1

Speed of sound through common materials

| Material | V (m/sec) |
| --- | --- |
| Acrylic (Perspex) | 2730 |
| Aluminum | 6320 |
| Beryllium | 12900 |
| Brass | 4430 |
| Copper | 4660 |
| Diamond | 18000 |
| Fiberglass | 2740 |
| Glycerin | 1920 |
| Inconel ® | 5820 |
| Iron, Cast (soft) | 3500 |
| Iron, Cast (hard) | 5600 |
| Molybdenum | 6250 |
| Nickel, pure | 5630 |
| Silicon | 9620 |
| Silicone | 1485 |
| Titanium | 6100 |
| Tungsten | 5180 |
| Water (20° C.) | 1480 |
| Zinc | 4170 |

Embodiments of the present invention provide a waveguide that is configured to focus ballistic shockwaves by harnessing the propagation speed of an acoustic wave through different materials by controlling the geometry and the materials forming the waveguide through which the ballistic shockwave is travelling so as to focus the ballistic shockwaves at a focal zone.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a schematic block diagrams of an exemplary system according to embodiments the present invention;

FIG. 1B-D are schematic illustrative diagrams of an exemplary ballistic shockwave focusing waveguide according to embodiments of the present invention;

FIG. 2A-C are schematic illustrative diagrams of an exemplary surface of the ballistic shockwave focusing waveguide according to embodiments of the present invention.

DESCRIPTION OF THE PREFERRED EMBODIMENTS

Figure 3:
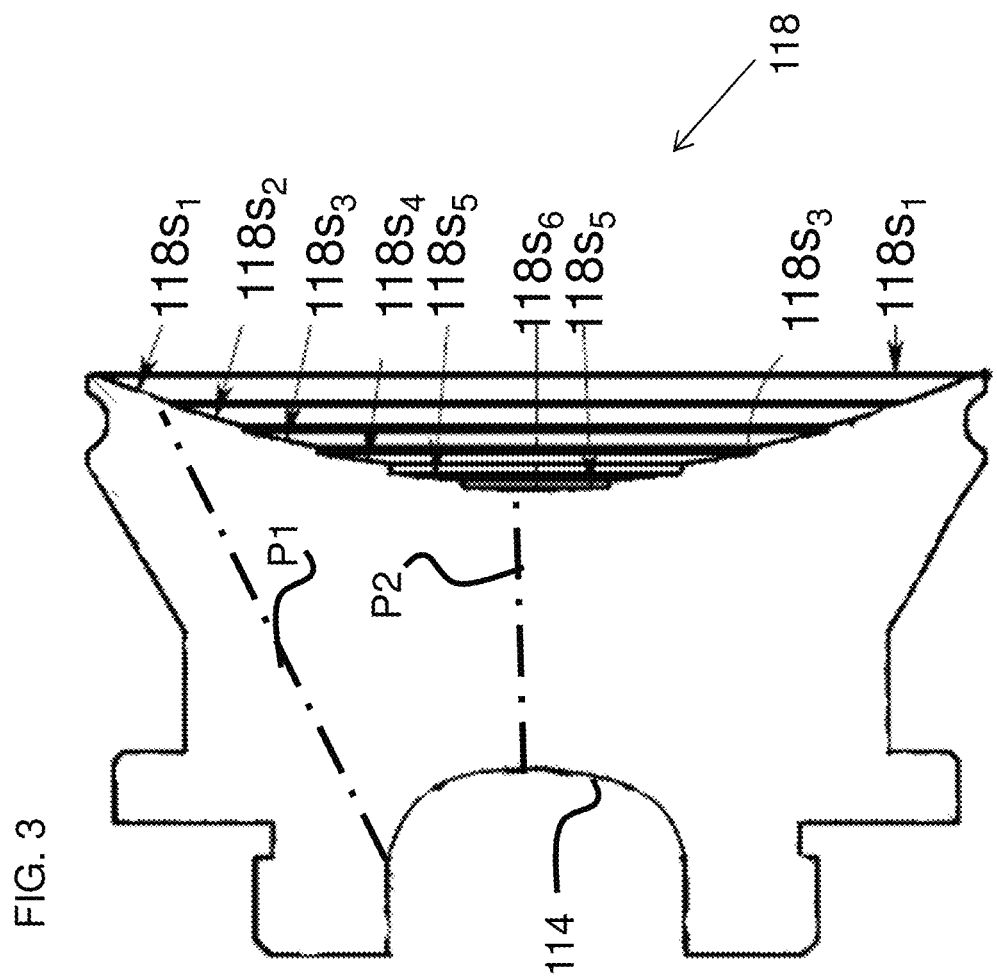
FIG. 3 is a schematic diagram of an exemplary surface of the ballistic shockwave focusing waveguide according to embodiments of the present invention.

The principles and operation of the present invention may be better understood with reference to the drawings and the accompanying description. The following figure reference labels are used throughout the description to refer to similarly functioning components are used throughout the specification hereinbelow.

50 body tissue;
F shockwave focal zone;
F1,F2, focal propagation lines
P1,P2 waveguide propagation lines;
L1,L2 fluid propagation lines;
T1,T2 tissue propagation lines;
100 shockwave system;
101 shockwave device;
105 projectile;
110 ballistic shockwave focusing waveguide;
112 distal portion/shockwave generating portion;
114 shockwave generating surface;
115 body;
115c membrane coupling member;
115s peripheral/external surface;
116 proximal portion;
118 focusing surface;
118a,b annular rings;
118s angled surfaces;
120 fluid filled membrane/sac
122 membrane;
124 fluid;

FIG. 1 A shows a schematic block diagram of a system 100 for providing shockwave treatment to the human or animal body. System 100 is characterized in that it is configured to provide ballistic shockwave treatment that is focus to a focal zones.

Shockwave treatment system 100 comprises a ballistic shockwave generating device 101, a ballistic shockwave focusing waveguide 110 and a fluid filled membrane 120.

Shockwave generating device 101 is provided in the form of a ballistic shockwave generating device utilized to propel a projectile 105 by utilizing a gaseous source, more preferably a high pressure source, to accelerate the projectile.

System 100 may optionally be utilized with an imagery system, for example medical imagery in the form of an ultrasound system, to facilitate locating and identifying a targeted treatment area for identifying the focal zone. Optionally imagery system may be provided in any form as is known in the art for example including but not limited to ultrasound, CT, MRI, Doppler Ultrasound, or the like.

Preferably shockwave generating device 101 may be fit with appropriate mechanical components, sensors, electronics, controls and processing capabilities as is known in the art for shockwave generating devices, and in particular ballistic shockwave generating devices.

Ballistic shockwave device 101 provides for producing high pressure extracorporeal focused ballistic shockwaves the system comprising: a projectile accelerating portion (not shown) coupled to a focusing waveguide 110 and a fluid filled membraned and/or sac 120. Waveguide 110 provides for channeling and/or routing the generated ballistic shockwaves onto the fluid filled membrane 120 in a focused manner such that they will reach the targeted focus zone in a focused manner within a time window of up to about 4 micro seconds and more preferably within a 1 microsecond time window.

Preferably the projectile accelerating portion (not shown) provides for accelerating a projectile 105 against a portion of waveguide 110 so as to generate a collision therebetween sufficient to generate a ballistic shockwave. Therein the ballistic shockwave is generated by a collision between an accelerated projectile 105 disposed within the projectile accelerating portion against a shockwave generating portion 112 of waveguide 110. The generated shockwaves propagate through the waveguide 110 toward its focusing surface 118 and thereafter onto the fluid filled membrane and/or sac 120 so as to allow transfer onto tissue to be treated. Most preferably the liquid filled membrane 120 comprises a fluid that lends for transferring the shockwaves onto the treated tissue, as is known in the art.

Shockwave generating device 101 is preferably provided in the form of a ballistic shockwave generating device that is adept at producing high-pressure shockwaves by accelerating a projectile 105 under high pressure through a projectile accelerator (not shown) toward shockwave generating portion 112 to produce high-pressure shockwaves.

Device 101, projectile 105 and shockwave generating portion 112 are provided from materials configured to allow for repeated collision to generate the high-pressure shockwaves.

Most preferably generating portion 112 is provided from metals and/or metallic alloys, that are configured to endure and withstand repeated collision with projectiles under high pressure, and sufficient to produce high pressure shockwaves.

Most preferably generating portion 112 is shaped and sized so as to allow it to endure and withstand repeated collision with projectile 105 under high pressure, while allowing for producing high pressure shockwaves. Preferably generating portion 112 is configured according to the shape and size of projectile 105. Preferably generating portion 112 comprises a distal end surface 114 that is provided in a concave configuration that matches the shape of projectile 105, for example as shown in FIG. 1BA-D. The concave configuration of surface 114 provides for optimizing shockwave production, and for matching the shape of projectile 105.

FIG. 1B shows a schematic illustration of projectile 105 and waveguide 110 prior to impact sufficient for generating a ballistic shockwave. FIG. 1C shows the impact between projectile 105 and waveguide 110 and generation of shockwaves P1, P2. FIG. 1D shows the propagation of shockwaves P1,P2 through waveguide 110, into liquid filled membrane 120 in the form of shockwave L1,L2 and finally onto the focal zone within tissue 50 shown as T1,T2, therein showing as shockwave travelling through waveguide 110 are focused to reach focal zonal F at a focal distance $F_L$.

Waveguide 110 comprises a body 115 including a distal portion 112 and a proximal portion 116.

Body 115 may assume any shape and more preferably provided in the form of a trapezoidal cylinder having a first end diameter about distal portion 112 that is smaller than a second end diameter about proximal portion 116. Body 115 defines an external peripheral surface 115s.

Distal portion 112 provides a shockwave generation portion including a distal end surface 114 provided for generating ballistic shockwaves by way of collision with projectile 105, as described above. Most preferably distal end surface 114 is configured to match the curvature and shape of projectile 105 so as to generate a ballistic shockwave in the most efficient manner as is known in the art. Surface 114 is preferably a concave surface configured to match the convex external surface of projectile 105.

Proximal portion 116 is continuous with distal portion 112 having a proximal end surface 118 defining a focusing surface for waveguide 110. Preferably focusing surface 118 is configured to focus shockwaves P1,P2 as they transition from proximal portion 116 to fluid filled membrane 120. Most preferably surface 118 is configured so as to allow the transition of shockwaves P1, P2 while focusing the shockwaves into liquid filled membrane 120 shown as L1,L2. Therein surface 118 allows for the routing of shockwaves P1,P2 to shockwaves L1, L2 due to the transition from a solid surface of the waveguide to the liquid environment of the liquid filled sac 120. Most preferably surface 118 is configured so as to allow the focusing by way of routing of shockwaves P1 to L1 and P2 to L2.

Similarly, the transition of shockwaves L1,L2 to T1, T2 at focal zone F within targeted tissue 50 is generally less pronounced as the fluid 124 in sac 120 and biological tissue 50 behave in the same manner.

Embodiments of the present invention provide for the focusing surface 118 for focusing a shockwave generated by ballistic shockwave device. Surface 118 is configured so as to ensure that the travel time of all shockwaves P1, P2 propagating through waveguide 110 to focal zone 'F' is provided at controlled time such that shockwaves T1,T2 reach focal zone 'F' at about the same time and more preferably within a time window of up to about 4 microseconds and more preferably up to about 1 microseconds.

Surface 118 provides for controlling the timing of shockwaves P1 and P2 as they travel at a uniform speed through body 115 however P1 travels along a longer pathway than does P2. Therefore P1 and P2 would not reach surface 118 at the same time and therefore could not be focused. Accordingly embodiment of the present invention overcome this problem by configuring surface 118 to overcome the timing discrepancy between P1 and P2. Accordingly, embodiments of the present invention provide for compensating for the differences between P1 and P2 by controlling at least one of the following:

a) the surface geometry of focusing surface 118; and/or b) providing a surface 118 that is composed of a plurality of materials having variable acoustic propagation speeds.

Both solution provided so as to ensure that shockwaves P1, P2 reach surface 118 substantially synchronically and/or simultaneously within a given time window of up to about 4 microseconds and more preferably up to about 1 microseconds so as to allow for focusing shockwaves P1 and P2 toward focal point 'F'.

In embodiments the waveguide 110 may be configured to produce focused ballistic shockwaves at a focal distance of up to about 30 meters. Optionally the focal distance may be configured to be from 1 centimeter up to about 10 centimeters. Optionally the focal distance may be configured to be from 1 centimeter up to about 50 centimeters. Optionally the focal distance may be configured to be from 30 centimeter up to about 250 centimeters. Optionally the focal distance may be configured to be from 1 meter up to about 30 meters. In embodiments the external diameter of the focusing surface 118 may be configured to be up to about 5 meters. In embodiments the external diameter of the focusing surface 118 may be configured to be from about 1 centimeter up to about 20 centimeters. In embodiments the external diameter of the focusing surface 118 may be configured to be from about 15 centimeters up to about 55 centimeters. In embodiments the external diameter of the focusing surface 118 may be configured to be from about 1 meter up to about 5 meters.

FIGS. 1C and 1D show the progression of a ballistic shockwave from its generation P1, FIG. 1C, to its delivery at focal zone F, FIG. 1D, across a focal length $F_L$. The waveguide according to embodiments of the present invention is configured for focusing the ballistic shockwave as it propagates through waveguide 110 onto fluid filled sac 120 and finally tissue 50 at focal zone 'F'. The propagation of shockwaves P1,P2 to L1,L2 and finally T1,T2 as they transition from waveguide to liquid filled sac and finally onto tissue is provided by the configuration of focusing surface 118.

Liquid filled membrane 120, as shown in FIG. 1D, comprises a membrane 122 and fluid 124. Membrane 122, shown as broken line, is fit over the proximal end of proximal surface 116 and therein covers focusing surface 118. Fluid 124 is disposed between membrane 122 and focusing surface 118 therein fluid 124 and surface 118 are in fluid communication. Most preferably membrane 122 is fit over the external surface 115s of body 115. In some embodiments body 115 may feature at least one or more membrane coupling recesses 115c for securely coupling and sealing membrane 122 onto body 115, as seen in FIG. 2A. Once surface 118 is covered with membrane 122 a fluid 124 may be introduced into the volume formed therebetween. Fluid 124 may for example include but is not limited to saline, water, medical gel, a gel, the like or any combination thereof as is known in the art.

Ballistic shockwave focusing waveguide 110 and any portion thereof is preferably made from solid phase materials, more preferably metals and/or metal alloys.

FIG. 2A shows a perspective view of waveguide 110 revealing an optional configuration for surface 118 that provides for focusing ballistic shockwaves by introduction of annular rings 118a,b.

As previously described surface 118 must compensate for the inherent time lag between parallel shockwaves P1,P2 travelling through waveguide body 115 between concave (generating) surface 114 to concave (focusing) surface 118. In order to compensate for the time lag surface 118 is configured as a concave surface that feature a plurality of annular rings 118a, 118b each ring having a uniform radius with respect to shockwave generating surface 114.

Annular rings 118a,b provide for focusing shockwave propagating through surface 118 in that each annular ring accounts for compensating for the time lag of the shockwave P1,P2 traveling therethough. For example, shockwaves, P1, corresponds to an outer annular ring 118a, while shockwave P2 corresponds to an internal annular ring 118b. Each annular ring is configured to ensure that the total travel time of P1 and L1 coincide with the total travel time of P2 and L2 such that the time it takes for T1 and t2 to reach focal zone 'F' is substantially synchronically and/or simultaneous and/or within a time window of up to about 4 microseconds and more preferably up to about 1 microseconds.

FIG. 2B shows an optional focusing configuration of surface 118 that is configured to provide a single focal point 'F', wherein all annular rings 118a,b are focused onto a single focal point 'F'. Most preferably for a single focal point 'F' each annular ring 118a,b is provided at a different angle determined according to Snell's law relating the material forming the waveguide 110 and the fluid 224. The angle is provided so as to ensure that the propagating shockwaves P1,P2 exits orthogonal to the surface angle of ring 118a and reaches focal point 'F' in a synchronized fashion most preferably within a time window of up to about 4 microseconds and more preferably up to about 1 microsecond.

FIG. 2C shows an optional multi-focusing configuration of surface 118 providing for a plurality of focal points F1-F5, wherein each annular ring 118a,b provide an individual corresponding focal point F1-F5. Focusing configuration as shown here is achieved by providing a stepwise configuration of annular rings 118a,b. Preferably the width of each stepwise annular ring is determined based on the allowable length of the time window, from up to 4 microseconds to about 1 microseconds, for synchronizing the arrival of the shockwaves P1,L1,T1 at the individual corresponding focal point F1.

FIG. 3 shows a cross sectional view of embodiment for a waveguide according to the present invention showing that the focusing surface 118 is configurable according to Snell's law so as to allow the propagation of shockwaves P1 and P2 to reach the focal point 'F' at the same time, as previously discussed. Accordingly in order to achieve this focusing surface 118 is provided with a plurality of angulated surfaces $118s_1$, $118s_2$, $118s_3$, $118s_4$, $118s_5$, $118s_6$, that are arranged in a concentric manner around surface 118. Most preferably the angulation of each of surfaces $118s_{1...n}$ is determined based on Snell's law so as to ensure that the proper routing into the fluid 124 is provided so as to focus at focal point 'F', accordingly, the plurality of angular surfaces 118s are configured so as to overcome the time lag between P1 and P2.

Most preferably the number of angulated surfaces is determined by the diameter of the focal zone. Most preferably the number of angulated surfaces is controllable and may be any number. In some embodiment the number of angulated surfaced may be determined by length of the time window required for shockwave synchronization, as previously described.

In another embodiment waveguide 110 may be provided from a plurality of materials having different acoustic propagation speeds so as to compensate for the time lag between ballistic shockwaves P1 and P2. For example a concentric annular ring configuration similar to that shown in FIG. 2A may be utilized however each ring may be formed from different materials having different acoustic propagation speed. For example the outermost ring would be provided from materials exhibiting slower acoustic propagation speed while innermost ring would be provided from materials exhibiting faster acoustic propagation speed.

EXAMPLE

Waveguide from Cooper Beryllium

The presently disclosed shockwave shaper takes advantage of the difference in the speed of sound propagation between different materials to produce a shockwaves shaper that has different propagation speeds along various portions. In a non-limiting example, Beryllium and copper may be used to construct the ballistic shockwaves waveguide 110 and in particular focusing surface 118.

The acoustic propagation speed through beryllium is 12,900 m/sec and the acoustic propagation speed through copper is 4660 m/sec. optionally other metals and/or materials may be added to the alloy for technical implementation reasons, for example including but not limited to aluminum, with an acoustic propagation speed of 6300 m/sec.

Alloys made of Beryllium and copper are widely used for many applications

Accordingly a ballistic shockwave waveguide may be composed from non-uniform proportions of Copper and Beryllium, so that the center portion of the construction—associated with shorter propagation path P2, will consist of a larger part of copper in the alloy, while the periphery of the construction associated with longer propagation path P1, will consist of a higher parts of beryllium in the alloy. Such a construct, with different ratios of beryllium and copper in regions of the ballistic shockwaves waveguide 110 will provide different propagation speeds in those regions—enabling to compensate for the different shockwave propagation speeds along the different shockwave paths P1, P2.

Most preferably, the geometry of the shockwave shaper is designed in accordance with the desired focal length and the distance between the middle and the periphery of the shockwave shaping portion.

In a non-limiting example, the construction of the ballistic shockwave waveguide provided from varying ratios of beryllium and copper may be implemented by sintering powders of beryllium and copper that are filled into a mold with the desired final shape and metal distribution.

Sintering is done in conditions that provide essentially isotropic and high density material construction. Such conditions can include sintering of the beryllium powder that is done into a liquid phase copper. In a non-limiting example, aluminum may be added to the copper to reduce its melting temperature, in order to achieve a stable liquid phase copper for the sintering process.

The powder ratios between beryllium, copper and aluminum are fed at the proportions that are calculated to generate the speed differences necessary to compensate for the different shockwave paths, P1,P2.

Proportions may vary widely, where copper may form less than 10% to 30% in weight, Beryllium and aluminum—up to 50% in weight.

In embodiments, the same principles of calculation and implementation may be used to produce ballistic shockwave waveguides that focus shockwave into several focal zones, that may exhibit the same depth, several focus areas each at different depth or a combination thereof.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

While the invention has been described with respect to a limited number of embodiments, it will be appreciated that many variations, modifications and other applications of the invention may be made.

What is claimed is:

1. A ballistic shockwave focusing waveguide for focusing shockwaves generated by a ballistic shockwave device to a focal zone, including a body formed from a solid material and configured to focus ballistic shockwaves at said focal zone having a constant predefined focal distance, the waveguide including:
   a. a first end defining a ballistic shockwave generating zone, having a curved surface shaped so as to match the curvature and radius of a shockwave generating projectile;
   b. a second end having a generally concave surface featuring a plurality of stepwise annular rings each annular ring having a uniform radius measured from said curved surface of said first end and wherein the uniform radius of each of said plurality of annular rings is configured according to:
      i. the acoustic propagation speed through said solid material forming said annular ring; and
      ii. said focal distance.

2. The waveguide of claim 1, wherein the number of said annular rings is determined based on a focal zone diameter.

3. The waveguide of claim 2, wherein the focal zone diameter decreases as the number of said annular rings increases.

4. The waveguide of claim 1, further comprises a fluid filled sac having a membrane covering said second end and wherein a volume formed between said second end and said membrane is filled with a fluid forming said fluid filled sac.

5. The waveguide of claim 4, wherein said waveguide is configured to deliver a generated shockwave to said focal zone within a time window determined based on a combined propagation speed of sound through said solid material forming said body and the fluid forming said fluid filled sac.

6. The waveguide of claim 5, wherein said generally concave surface is configured according to an index of refraction between said solid material forming said body and said fluid.

7. The waveguide of claim 4, wherein each of said annular rings are further configured to assume an angled surface, wherein the angle of the angulated surface is determined based on:
   i. the ratio of the acoustic propagation speed through said solid material and said fluid;
   ii. the focal distance of said waveguide; and
   iii. the distance from the angled surface to said first end.

8. The waveguide of claim 1, wherein said first end is a concave surface matching a convex end of a shockwave generating projectile of a ballistic shockwave generating system.

9. The waveguide of claim 1, wherein said body is shaped to assume a trapezoidal cylinder configuration, and wherein the external diameter of said first end is smaller than the external diameter of said second end.

10. The waveguide of claim 5, wherein said waveguide is configured to focus shockwaves onto said focal zone within a time window of up to 4 microseconds.

11. The waveguide of claim 10, wherein a width of said annular rings is configured according to the duration of said time window.

12. The waveguide of claim 5, wherein said waveguide is configured to focus shockwaves onto said focal zone within a time window of up to 1 microsecond.

13. The waveguide of claim 12, wherein a width of said annular rings is configured according to the duration of said time window.

14. The waveguide of claim 1, wherein said annular rings are configured to form a plurality of focal zones.

15. The waveguide of claim 1, wherein each of said annular rings is configured to form an individual focal zone.

16. The waveguide of claim 14, wherein a group of at least two or more of said annular rings are configured to form a focal zone.

17. The waveguide of claim 1, wherein each of said annular rings is provided from solid material having a different acoustic propagation speed.

18. The waveguide of claim 1, wherein a group of at least two or more of said annular rings are provided from solid materials having a different acoustic propagation speed.

19. The waveguide of claim 1, wherein said body is provided from a plurality of different solid materials having variable acoustic propagation speeds.

20. The waveguide of claim 1 further comprising a membrane configured to cover said second end of said body.

* * * * *